United States Patent [19]

Tanaka et al.

[11] Patent Number: 5,321,169
[45] Date of Patent: Jun. 14, 1994

[54] CYCLOHEXANE DERIVATIVES

[75] Inventors: Yasuyuki Tanaka; Haruyoshi Takatsu; Kiyohumi Takeuchi, all of Tokyo; Yuji Tamura, Saitama, all of Japan

[73] Assignee: Dainippon Ink and Chemicals, Inc., Tokyo, Japan

[21] Appl. No.: 60,040

[22] Filed: May 11, 1993

Related U.S. Application Data

[60] Continuation of Ser. No. 777,501, Oct. 17, 1991, abandoned, which is a continuation of Ser. No. 500,346, Mar. 28, 1990, abandoned, which is a division of Ser. No. 315,874, Feb. 27, 1989, Pat. No. 4,946,986.

[30] Foreign Application Priority Data

Feb. 29, 1988 [JP] Japan ................... 63-47041
Apr. 15, 1988 [JP] Japan ................... 63-91739
Jul. 26, 1988 [JP] Japan ................... 63-184527
Jan. 18, 1989 [JP] Japan ..................... 1-7656

[51] Int. Cl.$^5$ .................... C07C 25/18; C07C 15/12
[52] U.S. Cl. ................... 570/129; 558/412; 585/25
[58] Field of Search ............. 570/129; 585/25

[56] References Cited

U.S. PATENT DOCUMENTS

| 4,472,293 | 9/1984 | Sugimori et al. | 570/129 X |
| 4,477,369 | 10/1984 | Surimori et al. | 585/25 X |
| 4,545,922 | 10/1985 | Eidenschink et al. | 570/129 X |
| 4,814,523 | 3/1989 | Tanaka et al. | 570/129 |
| 4,946,986 | 8/1990 | Tanaka et al. | 558/411 |

FOREIGN PATENT DOCUMENTS

| 0062470 | 10/1982 | European Pat. Off. . | |
| 0084974 | 8/1983 | European Pat. Off. . | |
| 0099099 | 1/1984 | European Pat. Off. . | |
| 3717397 | 12/1988 | Fed. Rep. of Germany . | |
| 59-16841 | 1/1984 | Japan | 570/129 |
| 60-92228 | 5/1985 | Japan | 570/129 |

Primary Examiner—Joseph P. Brust
Attorney, Agent, or Firm—Armstrong, Westerman, Hattori, McLeland & Naughton

[57] ABSTRACT

A novel tetracyclic cyclohexylcyclohexene derivatives represented by formula:

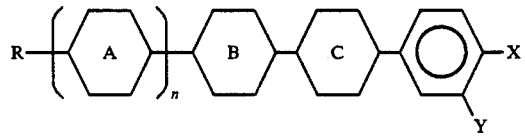

wherein

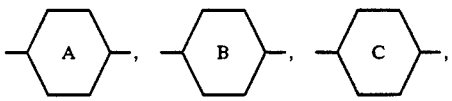

n, X and Y are as defined in the specifications, are disclosed. The compounds are useful as electroptic display materials.

12 Claims, No Drawings

CYCLOHEXANE DERIVATIVES

This application is a continuation of application Ser. No. 07/777,501 filed Oct. 17, 1991, now abandoned, which is a continuation of Ser. No. 07/500,346, filed Mar. 28, 1990, now abandoned, which is a division of Ser. No. 07/315,874, filed Feb. 27, 1989, now U.S. Pat. No. 4,946,986.

BACKGROUND OF THE INVENTION

The present invention relates to novel cyclohexylcyclohexene derivatives that are useful as electrooptic display materials.

Typical examples of liquid-crystal display cells include the dynamic scattering mode cell proposed by G. H. Heilmeier et al. in Appl. Phys. Letters, 13, 46 (1968), the field-effect mode cell proposed by M. Schadt et al. in Appl. Phys. Letters, 18, 127 (1971), and the quest-host mode cell proposed by G. H. Heilmeier et al. in Appl. Phys. Letters, 13, 91 (1968).

While various characteristics are required of liquid-crystal materials used in these liquid-crystal display cells, the most important one which must be shared by all display cells is that they have a nematic phase over a broad range of temperatures including room temperature. Many of the practically feasible liquid-crystal materials satisfying this requirement are usually prepared by mixing several or more components including a compound having a nematic phase at a temperature in the vicinity of room temperature and a compound having the nematic phase in the temperature range higher than room temperature. Many of such mixed liquid crystals commercially used today are at least required to have a nematic phase over the entire range of temperatures from −30° C. to +65° C. With the recent expansion in the fields of applications of liquid-crystal display cells, a need has arisen for the development of liquid-crystal materials in which the temperature range for the appearance of a nematic phase is extended to even higher levels. More recently, it has become necessary to develop a nematic liquid-crystal compound having a high N-I point, that is, temperature at which a transition occurs from nematic to isotropic liquid phase or vice versa.

To meet these needs, U.S. Pat. Nos. 4,422,951, 4,439,340 and 4,536,321, as well as European Patents 62,470 and 119,756 have proposed compounds such as 4-[4'(4''-substituted cyclohexyl)-cyclohexyl] substituted benzene that have N-I points around 200° C. Liquid-crystal compounds having a nematic phase in an even higher temperature range are described in U.S. Pat. Nos. 4,472,293 and 4,477,369, as well as European Patents 84,974 and 99,099; the compounds proposed in these patents include 4,4'-bis(4-substituted phenyl)-bicyclohexane, 4-substitutedz-{4'-[4''-(4''-alkylcyclohexyl)-cyclohexyl]cyclohexyl}-benzene, 4-alkyl-4''-(4-halogenophenyl)-octadecahydro-p-terphenyl and 4-alkyl-4''(3,4-difuorophenyl) octadecahydro-p-terphenyl and have N-I points around 300° C.

However, the compounds proposed in these prior patents suffer from the disadvantage that their C-N point (temperature at which a transition occurs from crystalline to nematic phase or vice versa) or S-N point (temperature at which a transition occurs from smectic to nematic phase or vice versa), which are the lower limits of the temperature range where a nematic phase occurs, are high.

If these compounds having high C-N or S-N points are added to nematic mixed liquid crystals which are commonly used in practice as host liquid crystals with a view to enhancing their N-I points, a crystalline or smectic phase will appear in the low-temperature range.

SUMMARY OF THE INVENTION

An object, therefore, of the present invention is to provide a novel liquid-crystal compound that has a high N-I point and a low C-N or S-N point.

This object of the present invention can be attained by a compound represented by the following general formula:

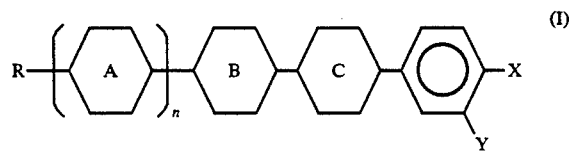

where R is a straight-chained alkyl group having 1-9 carbon atoms;

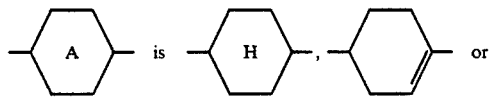

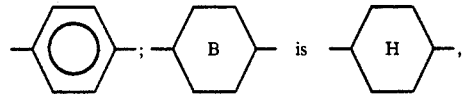

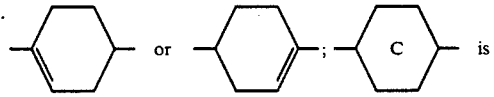

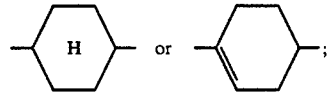

n is 0 or 1; when n=0, X is cyano group and Y is a hydrogen or fluorine atom; when n=1, X is a fluorine atom, a straight-chained alkyl group having 1-9 carbon atoms, and Y is a hydrogen or fluorine atom.

The compound of formula (I) of the present invention can be produced by one of the following methods:

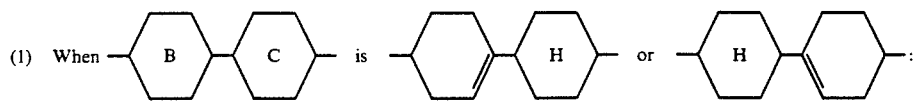

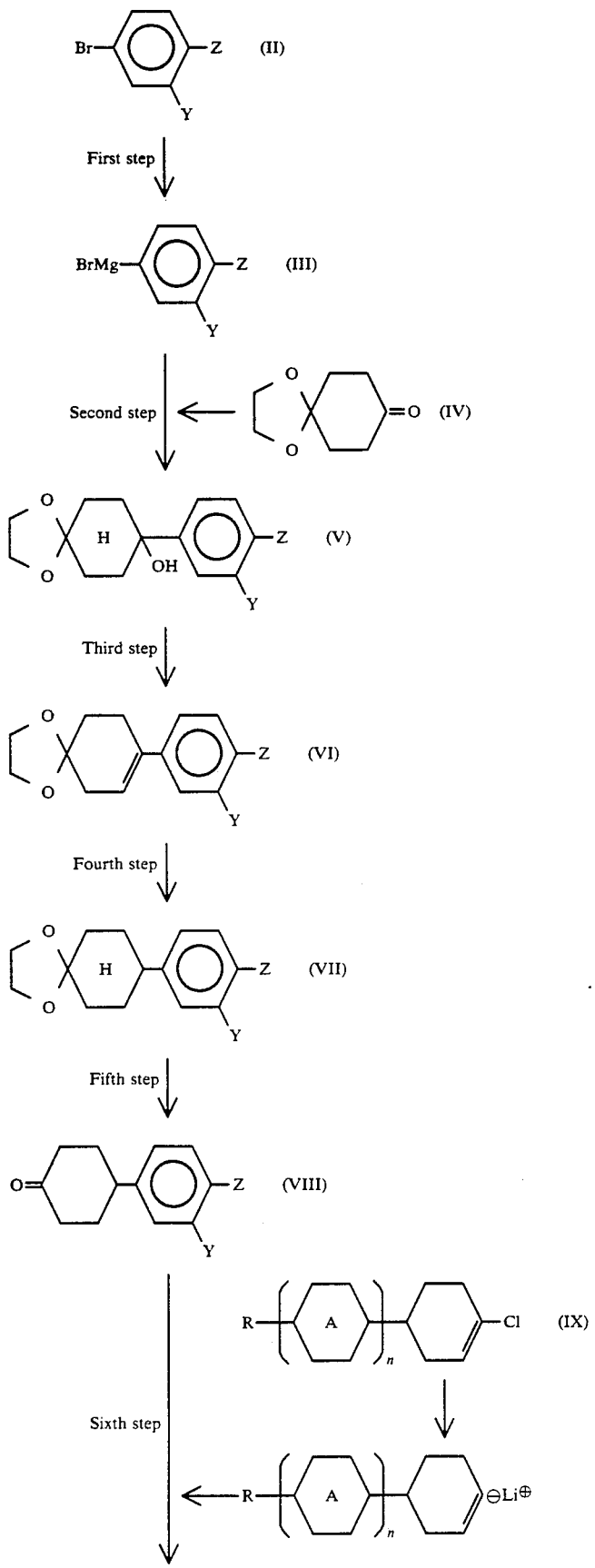

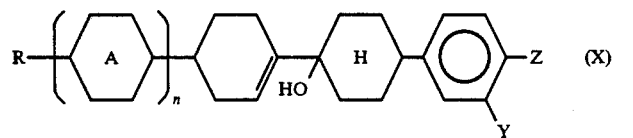 (X)
Seventh step ← (CH₃)₃SiI
HI ←
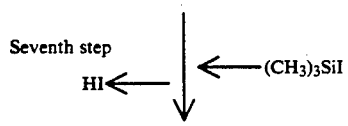
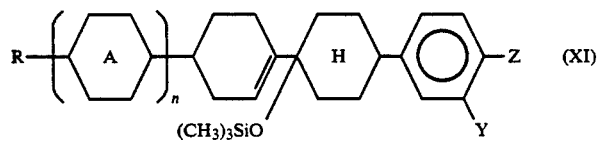 (XI)
(CH₃)₃SiOH ←
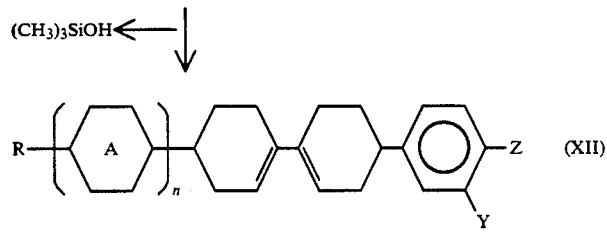 (XII)
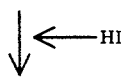 ← HI
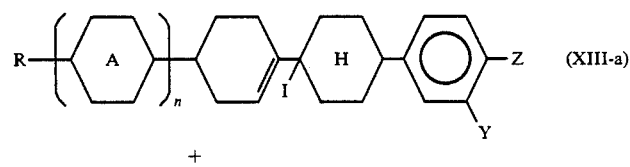 (XIII-a)
+
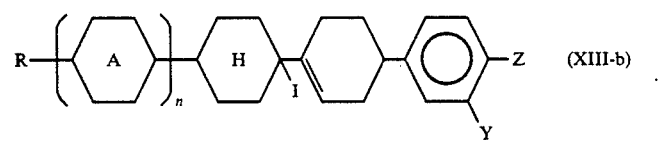 (XIII-b)
(CH₃)₃SiI + (CH₃)₃SiOH
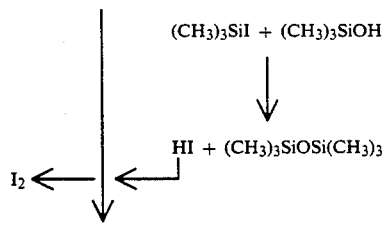
HI + (CH₃)₃SiOSi(CH₃)₃
I₂ ←
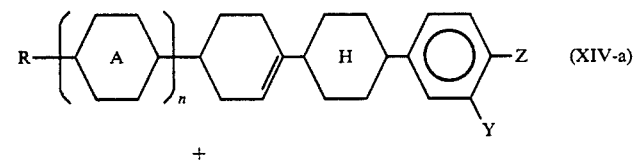 (XIV-a)
+
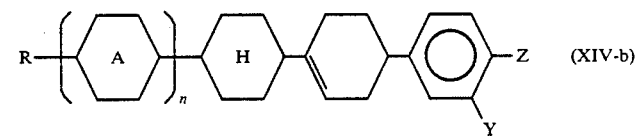 (XIV-b)
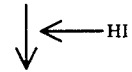 ← HI -continued
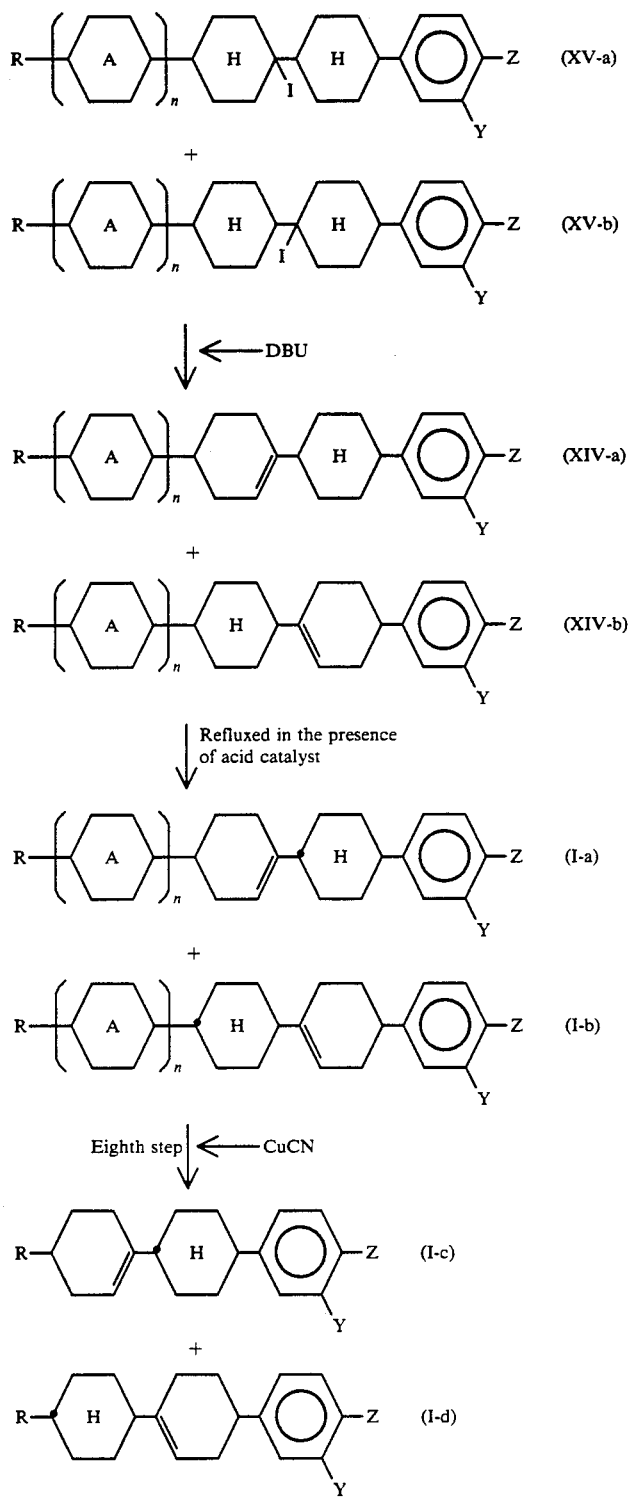
(in the reaction scheme described above,
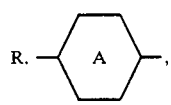
n and Y have the same meanings as defined for formula (I); and Z is a fluorine atom, a chlorine atom, a straight-chained alkyl or alkoxy group having 1-9 carbon atoms).

(2) When 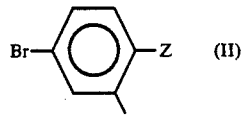 is  or 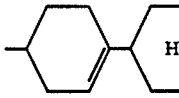:
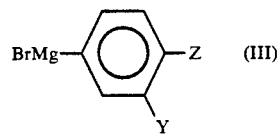 (II)
First step ↓
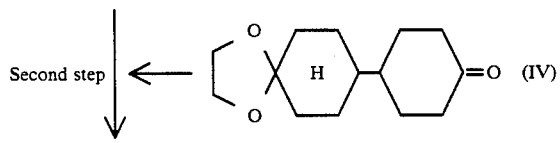 (III)
Second step ← 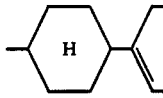 (IV)
↓
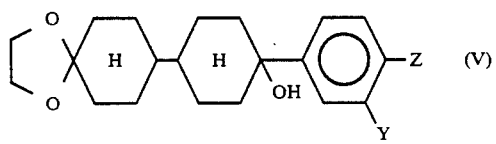 (V)
Third step ↓
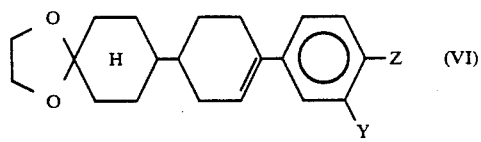 (VI)
Fourth step ↓
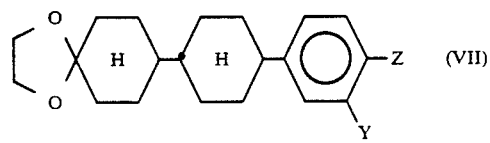 (VII)
Fifth step ↓

-continued
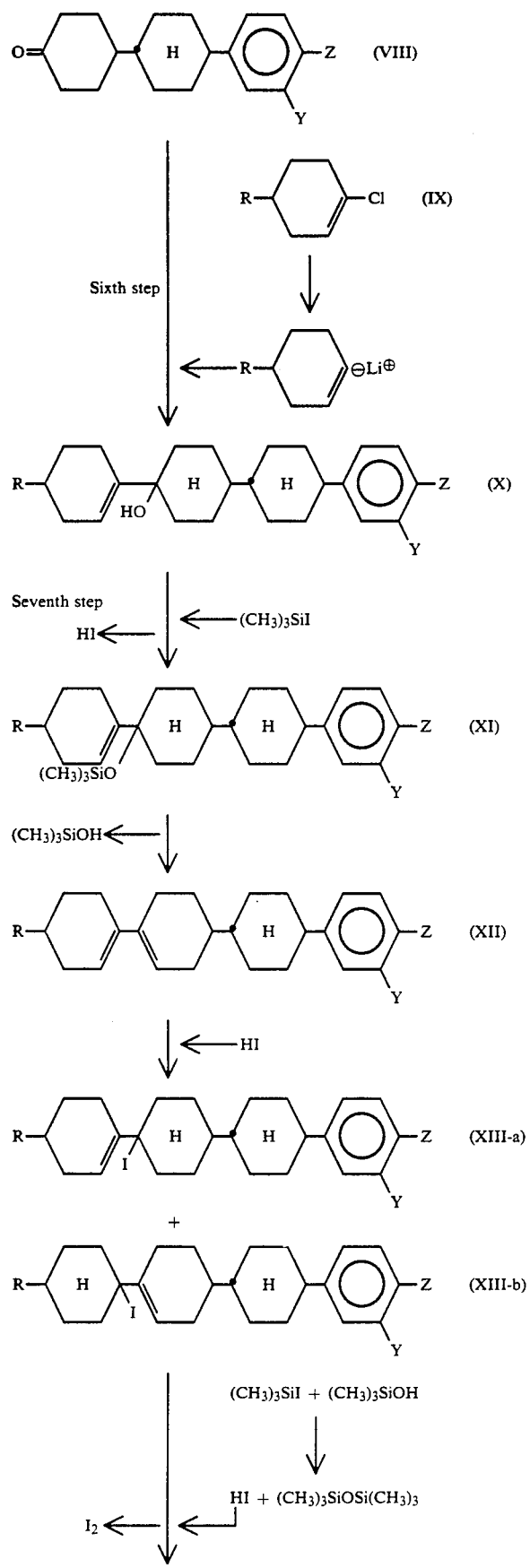

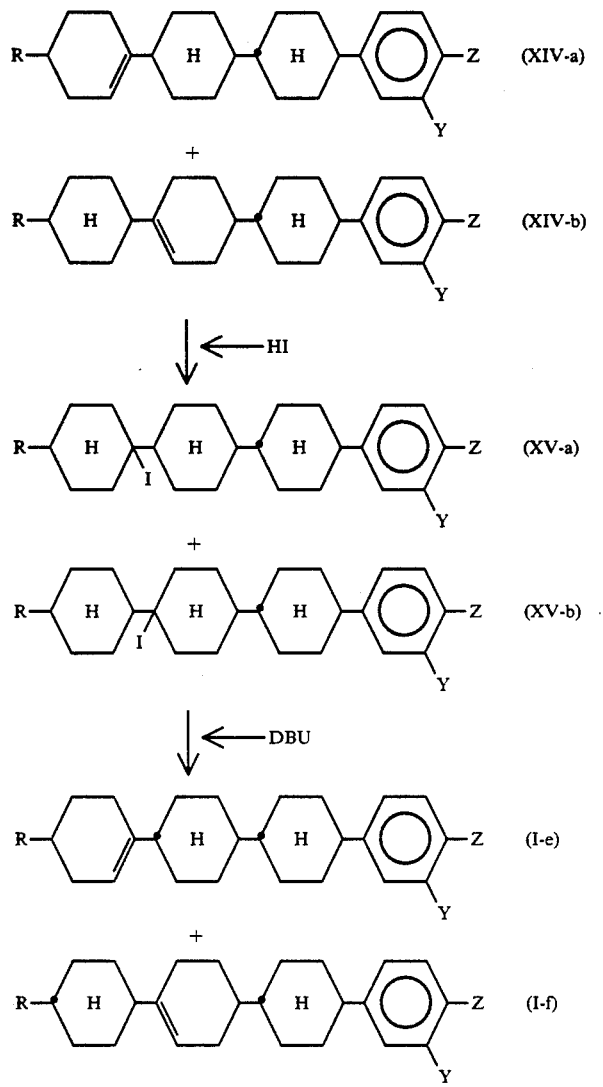

(in the reaction scheme described above,

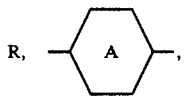

n and Y have the same meanings as defined for formula (I); and Z is a fluorine atom, a chlorine atom, a straight-chained alkyl or alkoxy group having 1–9 carbon atoms).

The individual steps of the process for producing the compound of formula (I) are described below in detail.

First step: A compound of formula (II) is reacted with a magnesium powder in an ether-based solvent such as anhydrous tetrahydrofuran (hereinafter abbreviated as THF) at 15°–30° C. for 1–2 hr to prepare a compound of formula (III).

Second Step: To a solution of the compound of formula (III), a solution of a compound of formula (IV) in anhydrous THF is added at 5 20-20° C. and the mixture is subjected to reaction at 10°–30° C. for 30 min to 1 hr; thereafter, the reaction product is decomposed with a saturated aqueous solution of ammonium chloride to prepare a compound of formula (V).

Third step: The compound of formula (V) is subjected to reaction in a water-insoluble inert solvent such as toluene for 0.1–8 hr under reflux in the presence of an acidic catalyst such as p-toluenesulfonic acid; after cooling the reaction mixture, the solvent layer is washed first with a saturated aqueous solution of sodium hydrogen carbonate, then with a saturated aqueous solution of sodium chloride; after drying, the solvent is distilled off and the crude reaction product is recrystallized from an alcoholic solvent such as ethanol to prepare a compound of formula (VI).

Fourth step: The compound of formula (VI) is dissolved in a water-insoluble inert solvent and catalytically reduced at 20°–80° C. for 6–30 hr at a hydrogen pressure of no more than 3 kg/cm$^2$ in the presence of a hydrogenation catalyst such as platinum oxide or Raney nickel to prepare a compound of formula (VII).

Fifth step: The compound of formula (VII) is dissolved in an inert solvent such as toluene and reacted with an acidic aqueous solution such as dilute sulfuric acid for 5–6 hr under reflux; after cooling the reaction mixture, the solvent layer is washed with water, dried and freed of the solvent by distillation; the crude reaction product is purified by column chromatography on silica gel and further purified by recrystallization from a mixed solvent of n-hexane and toluene to prepare a compound of formula (VIII).

Sixth step: A compound of formula (IX) is converted to a lithium salt by reaction with lithium in an ether-based solvent such as anhydrous diethyl ether under reflux for 2-9 h; to the lithium salt, a solution of the compound of formula (VIII) in an ether-based solvent such as anhydrous diethyl ether is added at $-20°$ C. to $+5°$ C. and reaction is performed at $5°-25°$ C. for 30 min; the reaction mixture is decomposed with water and the reaction product is extracted with toluene; the extract is washed with water, dried and freed of the solvent by distillation to prepare a compound of formula (X).

Seventh step: The compound of formula (X) is dissolved in n-hexane or toluene; the solution is added to an acetonitrile solution of iodo-trimethylsilane prepared from chlorotrimethylsilane and sodium iodide in acetonitrile and the mixture is subjected to reaction at $5°-10°$ C. for 30 min-1 h; in this way, a reaction mixture composed of compounds of formulas (XIV-a), (XIV-b), (XV-a) and (XV-b) is prepared from the compound of formula (X) via an intermediate composed of compounds of formulas (XII), (XIII-a) and (XIII-b).

To this reaction mixture, a base such as 1,8-diazabicyclo(5,4,0)undecene-7 (hereinafter abbreviated as DBU) is added and reaction is performed at $5°-30°$ C. for 5-20 hr so as to prepare compounds of formulas (XIV-a) and (XIV-b) from compounds of formulas IXV-a) and (XV-b), respectively. After adding water to the reaction mixture, the compounds of formulas (XIV-a) and (XIV-b) are extracted with toluene and the extracts are washed successively with dilute HCl, a saturated acidic aqueous solution of sodium hydrogen sulfite, a saturated aqueous solution of sodium hydrogen-carbonate and a saturated aqueous solution of sodium chloride; after drying, the solvent is distilled off from the extracts.

The mixture of compounds of formulas (XIV-a) and (XIV-b) is dissolved in an inert solvent such as toluene and subjected to reaction under reflux for 1-8 hr in the presence of an acidic catalyst such as p-toluenesulfonic acid, thereby isomerizing the cyclohexane ring from a cis- to trans-configuration; in this way, a mixture of compounds of formulas (I-a) and (I-b) or a mixture of compounds of formulas (I-e) and (I-f), all being within the scope of the present invention, is produced in high yield.

These mixtures are purified by column chormatography on silica gel and further purified by recrystallization n-hexane or from a mixed solvent of n-hexane and ethanol. Subsequently, the compounds of formulas (I-a) and (I-b) or the compounds of formulas (I-e) and (I-f) are isolated from the purified products by high-performance liquid chromatography. The isolated compounds are recrystallized from n-hexane or a mixed solvent of n-hexane and ethanol, thereby producing pure compounds of formulas (I-a), (I-b),(I-e) and (I-f) which are within the scope of the present invention.

Eighth step: A mixture of compounds of formulas (I-a) and (I-b) wherein Z is chlorine is dissolved in an aprotic polar solvent such as N-methyl-2-pyrrolidone (hereinafter abbreviated as NMP) and reacted with copper cyanide (CuCN) at $190°-200°$ C. for 8-12 hr. After cooling, the reaction mixture is added to 30% aqueous ammonia and the reaction product is extracted with toluene. The extract is washed successively with 30% aqueous ammonia, water, dilute HCl, a saturated aqueous solution of sodium hydrogen-carbonate and a saturated aqueous solution of sodium chloride. After drying, toluene is distilled off from the extract. The crude reaction product is purified by column chromatography on silica gel and further purified by recrystallization from ethanol to prepare a mixture of compounds of formulas (I-c) and (I-d) By high-performance liquid chromatography, the compounds of formulas (I-c) and (I-d) are isolated from the mixture and recrystallized from ethanol to produce pure compounds of formulas (I-c) and (I-d) within the scope of the present invention.

Typical examples of the compounds of formula (I) thus produced are listed in Table 1 below together with their transition temperatures.

TABLE 1

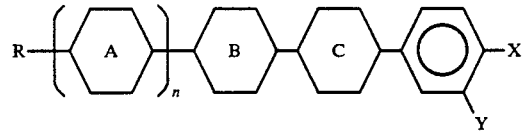

| No. | Structural formula | Transition temperature (°C.) |
|---|---|---|
| 1 | n-C₃H₇—⟨H⟩—⟨⟩—CN | 69 (C ⟶ N)<br>183 (N ⇌ I) |
| 2 | n-C₃H₇—⟨H⟩—⟨⟩—CN | 62 (C ⟶ N)<br>167 (N ⇌ I) |
| 3 | n-C₃H₇—⟨H⟩—⟨⟩—CN (F) | 51 (C ⟶ N)<br>148 (N ⇌ I) |

TABLE 1-continued $$R-\left(\boxed{A}\right)_n-\boxed{B}-\boxed{C}-\bigcirc-X$$
$$\phantom{xxxxxxxxxxxxxxxxxxxxxxxxxx}Y$$

| No. | Structural formula | Transition temperature (°C.) |
|-----|-------------------|------------------------------|
| 4 | n-C₃H₇–[H]=[ ]–⟨CN, F⟩ | 45 (C → N); 133 (N ⇄ I) |
| 5 | CH₃–⟨ ⟩–[ ]=[H]–⟨ ⟩–CH₃ | 154 (C → N); 243 (N ⇄ I) |
| 6 | n-C₄H₉–[H]–[ ]=[H]–⟨F, F⟩ | 60 (C → S); 160 (S ⇄ N); 244 (N ⇄ I) |
| 7 | n-C₄H₉–[H]–[H]–[ ]=⟨F, F⟩ | 64 (C → S); 170 (S ⇄ N); 238 (N ⇄ I) |
| 8 | n-C₃H₇–[ ]=[H]–[H]–⟨ ⟩–CH₃ | 240 (S ⇄ N); 290 (N ⇄ I) |
| 9 | n-C₃H₇–[H]–[ ]=[H]–⟨ ⟩–CH₃ | 250 (S ⇄ N); 282 (N ⇄ I) |
| 10 | n-C₄H₉–[ ]=[H]–[H]–⟨F, F⟩ | 148 (S ⇄ N); 241 (N ⇄ I) |
| 11 | n-C₄H₉–[H]–[ ]=[H]–⟨F, F⟩ | 158 (S ⇄ N); 235 (N ⇄ I) |

(C, crystalline phase; S, smectic phase; N, nematic phase; I, isotropic liquid phase.)

The compound of formula (I) of the present invention is a nematic liquid-crystal compound having a very weak positive, a positive or a weak negative anisotropy in dielectric constant. Therefore, when mixed with another nematic liquid-crystal compound having a negative or weak positive anisotropy in dielectric constant, the compound of the present invention can be used as the constituent material of a dynamic scattering mode display cell. Alternatively, it may be used as the constituent material of a field-effect mode display cell when mixed with another nematic liquid-crystal compound having a strong positive anisotropy in dielectric constant.

Preferred examples of such compounds that can be used in admixture with the compound of formula (I) are listed below: 4'-substituted phenyl 4-substituted benzoate ester, 4'-substituted phenyl 4-substituted cyclohexanecarboxyate ester, 4'-substituted biphenyl 4-substituted cyclohexanecarboxyate ester, 4'-substituted phenyl 4-(4-substituted cyclohexanecarbonyloxy)benzoate ester, acid 4'-substituted phenyl 4-(4-substituted cyclohexyl)benzoate ester, 4'-substituted cyclohexyl 4-(4-substituted cyclohexyl)-benxoate ester, 4-substituted 4'-substituted biphenyl, 4-substituted phenyl-4'-substituted cyclohexane, 4-substituted 4''-substituted terphenyl, 4-substituted biphenyl 4'-substituted cyclohexane, and 2-(4-substituted phenyl)-5-substituted pyrimidine.

Known compounds that are similar in chemical structure to the compound of formula (I) of the present invention and which have been proposed for use as materials that increase the N-I points of mixed liquid crystals are listed below in Table 2 together with their respective transition points.

compound (a), compound Nos. 3 and 4 with known compound (b), compound No. 5 of the present invention with known compound (c), and compound Nos. 6, 7, 10 and 11 with known compound (f), one will be able to understand the following: the compound of formula (I) of the present invention has a sufficiently high N-I point to be useful in the preparation of mixed liquid crystals that can be driven at high temperatures; the temperature range in which the compound of formula (I) exhibits a nematic phase than that of known compounds having a similar structure; and the compound of formula (I) has a C-N or S-N point that is much lower than those of known compounds having similar structures.

Table 3 shows the N-I points of two mixed liquid crystals (B) and (C) containing 90 wt % of mixed liquid crystal (A) which is commercially used today as the host liquid crystal of nematic liquid-crystal materials; liquid crystal (B) additionally contains compound Nos. 8 and 9 of formula (I) (see Table 1) in respective amounts of 5 wt %, and liquid crystal (C) additionally

TABLE 2

| No. | Structural formula | Transition temperature (°C.) |
|---|---|---|
| (a) | n-$C_3H_7$—[H]—[H]—[⬡]—CN (U.S. Pat. No. 4,439,340) | 73 (C → S) <br> 81 (S ⇌ N) <br> 243 (N ⇌ I) |
| (b) | n-$C_3H_7$—[H]—[H]—[⬡]—CN, F (U.S. Pat. No. 4,536,321) | 54 (C → S) <br> 90 (S ⇌ N) <br> 207 (N ⇌ I) |
| (c) | $CH_3$—[⬡]—[H]—[H]—[⬡]—$CH_3$ (U.S. Pat. No. 4,422,951 and EP 62,470) | 190 (C → N) <br> 269 (N ⇌ I) |
| (d) | $C_2H_5$—[H]—[H]—[H]—[⬡]—$CH_3$ (U.S. Pat. No. 4,477,369 and EP 84,974) | 71 (C → S) <br> 254 (S ⇌ N) <br> 293 (N ⇌ I) |
| (e) | n-$C_3H_7$—[H]—[H]—[H]—[⬡]—F (U.S. Pat. No. 4,472,293 and EP 99,099) | 106 (C → S) <br> 238 (S ⇌ N) <br> 279 (N ⇌ I) |
| (f) | n-$C_4H_9$—[H]—[H]—[H]—[⬡]—F, F (U.S. Pat. No. 4,472,293 and EP 99,099) | 72 (C → S) <br> 217 (S ⇌ N) <br> 299 (N ⇌ I) |

When one compares Table 1 and 2, in particular compound Nos. 1 and 2 of the present invention with known contains compound Nos. 10 and 11 of formula (I) (also see Table 1) in respective amounts of 5 wt %. As a comparison, the N-I point of mixed liquid crystal (A) is also shown in Table 3. This liquid crystal (A) consists of the following components:

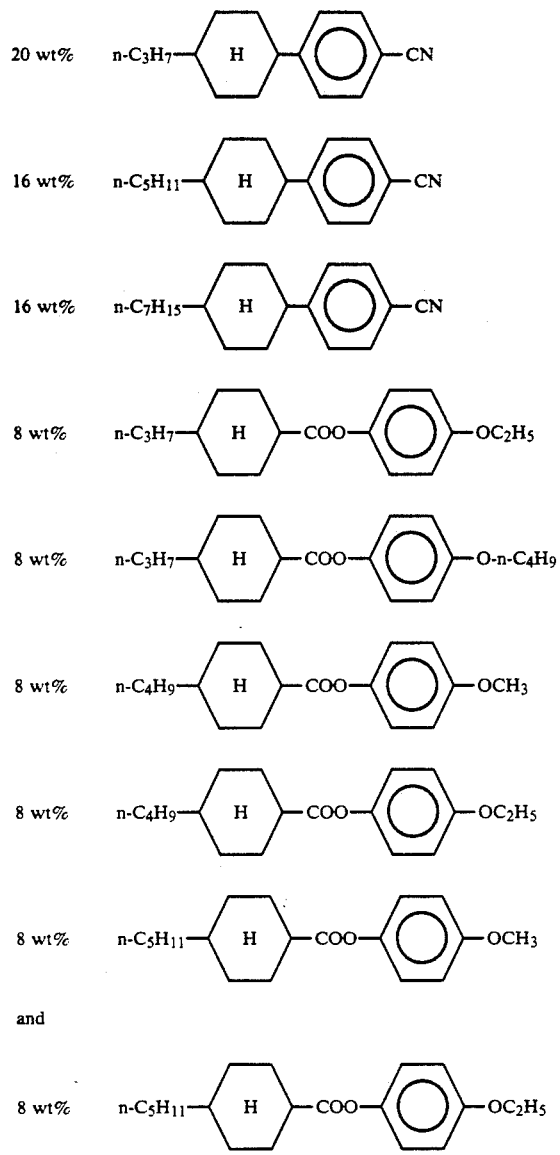

and

TABLE 3

| Mixed liquid crystal | N-I point (°C.) |
|---|---|
| (A) | 54.0 |
| (B) | 75.5 |
| (C) | 70.0 |

One can see from the data shown in Table 3 that the compound of formula (I) is effective in achieving a marked increase in the N-I point of mixed liquid crystal (A).

The following examples are provided for the purpose of further illustrating the present invention but are in no way to be taken as limiting.

EXAMPLE 1

A solution of p-dibromobenzene (53.0 g, 0.225 mol) in anhydrous THF (210 ml) was added dropwise to a magnesium powder (6.00 g, 0.247 gram atom) with stirring at 15°-23° C. By further reaction at room temperature (25° C.). for 2 hr, a compound represented by the formula)

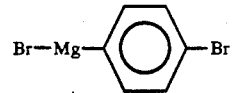

was obtained.

A solution of a compound of the formula

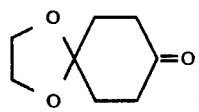

O(26 g, 0.171 mol) in anhydrous THF (53 ml) was added dropwise to the above prepared Grignard reagent with stirring at 10°-15° C., followed by reaction for another 30 min at room temperature. After completion of the reaction, the reaction mixture was added to a saturated aqueous solution of ammonium chloride and the reaction product was extracted with toluene. The extract was washed with water and dried. When the solvent was distilled off from the dried solution, a crude product containing a compound having the structure shown below was obtained in an amount of 51.7 g:

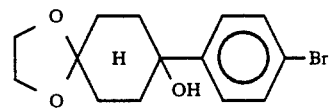

This crude product was dissolved in toluene (260 ml) and p-toluenesulfonic acid monohydrate (0.26 g, 0.0014 mol) was added to the solution and subjected to a dehydration reaction under reflux for 4 h with stirring. After cooling the reaction mixture, the toluene layer was successively washed with a saturated aqueous solution of sodium hydrogencarbonate and a saturated aqueous solution of sodium chloride, and subsequently dried. The reaction product obtained by distilling off toluene was recrystallized from ethanol to obtain the pure form of a compound having the structure shown below in an amount of 42.0 g (0.142 mol); yield 83%:

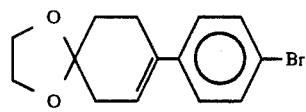

This compound (20.0 9, 0.0678 mol) was dissolved in toluene (50 ml). A catalytic amount of platinum oxide was added to the solution, which was stirred at ambient temperature and atmospheric pressure to perform a hydrogenation reaction. After completion of the reaction, the reaction mixture was filtered to remove the catalyst. By distilling off toluene from the filtrate, a crude product containing a compound having the structure shown below was obtained in an amount of 19.3 g:

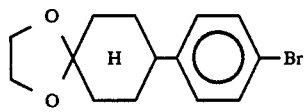

This crude product was dissolved in toluene (70 ml) and 10% sulfuric acid (50 ml) was added to the solution, followed by reaction with stirring for 6 h under reflux. After completion of the reaction, the reaction mixture was cooled and the toluene layer was washed with water and dried, followed by removal of toluene by distillation. The obtained crude product was purified by column chromatography on silica gel and further purified by recrystallization from a mixed solvent of n-hexane and toluene to obtain 10.3 g (0.0408 mol) of a compound having the structure shown below; m.p. 60 C. and yield 60%:

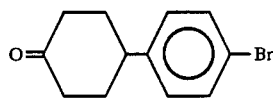

In the next step, a compound (1.7 g, 0.011 mol) represented by the formula

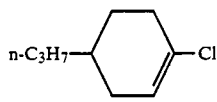

;was dissolve in anhydrous diethyl ether (6 ml). Lithium (0.15 g, 0.022 gram atom) was added to the solution, which was stirred for reaction under reflux for 4 h. After completion of the reaction, the reaction mixture was cooled and an anhydrous diethyl ether solution (7 ml) of the previously obtained compound of the formula

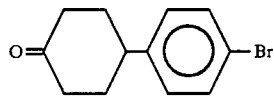

(2.2 g, 0.00087 mol) was added dropwise to this reaction mixture at −15° to −5° C., followed by reaction at room temperature for 30 min. After adding the reaction mixture to cold water, the reaction product was extracted with toluene and the extract was washed with water and dried. By distilling off the solvent, a crude product containing a compound having the structure shown below was obtained in an amount of 3.3 g:

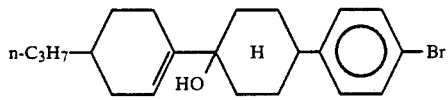

Sodium iodide (4.6 g, 0.031 mol) was dissolved in acetonitrile (18 ml) and chlorotrimethylsilane (3.4 g, 0.031 mol) was added dropwise to this solution. To the resulting solution, a n-hexane solution (7 ml) of the previously obtained crude product was added dropwise with stirring at 5°–10° C., followed by reaction at the same temperature for 30 min. To the reaction mixture, DBU (5.3 g, 0.035 mol) was added dropwise at 5°–17° C. and stirred at room temperature (25° C.) for 18 h. Water was added to the reaction mixture and the reaction product was extracted with toluene. The extract was successively washed with dilute HCl, a saturated acidic aqueous solution of sodium sulfite, a saturated aqueous solution of sodium hydrogen-carbonate and a saturated aqueous solution of sodium chloride, and subsequently dried. By distilling off the solvent, a crude reaction product was obtained.

This crude reaction product was dissolved in toluene (6 ml) and p-toluenesulfonic acid monhydrate (0.033 g, 0.00017 mol) was added to the solution, followed by stirring to effect isomerization under reflux for 3 h. After cooling the reaction mixture, the toluene layer was successively washed with a saturated aqueous solution of sodium hydrogencarbonate and a saturated aqueous solution of sodium chloride, and subsequently dried. By distilling off toluene, a crude reaction product was obtained. This crude reaction product was purified by recrystallization from ethanol containing a small amount of n-hexane. As a result, a mixture of two compounds having the structures shown below was obtained in an amount of 1.8 g (0.0050 mol); yield 57%. This mixture showed a nematic phase between 91° and 123° C.:

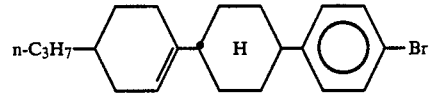

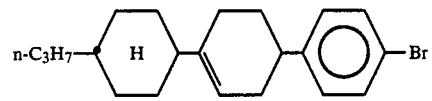

In the next step, this mixture was dissolved in NMP (5 ml) and CuCN (0.46 g, 0.0051 mol) was added to the solution, followed by stirring to effect a reaction at 190°–200° C. for 11 hr. The reaction mixture was cooled and added to 30% aqueous ammonia. Thereafter, the reaction product was extracted with toluene. The extract was successively washed with 30% aqueous ammonia, water, dilute HCl, a saturated aqueous solution of sodium hydrogencarbonate, and a saturated aqueous solution of sodium chloride, and subsequently dried. By distilling off toluene from the dried extract, a crude reaction product was obtained in an amount of 1.5 g. This crude reaction product was purified by column chromatography on silica gel and further purified by recrystallization from ethanol so as to obtain a mixture (1.0 g, 0.003 mol) of two compounds having the structures shown below; yield 66%. this mixture showed a nematic phase between 61° and 177° C.

By high-pressure liquid chromatography, the individual components of the mixture were isolated. Thereafter, the isolated components were purified by recrystallization from ethanol to obtain the desired compounds.

| | Transition temperature | |
|---|---|---|
| n-C₃H₇—⬡—(H)—⌬—CN | 51° C. | (C ⟶ N) |
| | 148° C. | (N ⇌ I) |
| n-C₃H₇—(H)—⬡—⌬—CN | 62° C. | (C ⟶ N) |
| | 167° C. | (N ⇌ I) |

EXAMPLE 2

The procedures of Example 1 were repeated except that p-dibromobenzene was replaced by 2-fluoro-1,4-dibromobenzene (57.2 g, 0.225 mol). As a result, compounds having the structures shown below were individually obtained:

| | Transition temperature | |
|---|---|---|
| 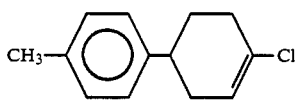 | 51° C. | (C ⟶ N) |
| | 148° C. | (N ⇌ I) |
| 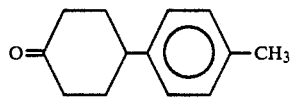 | 45° C. | (C ⟶ N) |
| | 133° C. | (N ⇌ I) |

EXAMPLE 3

A compound of the formula

CH₃—⌬—⬡—Cl (5.0 g, 0.024 mol) was dissolved in anhydrous diethyl ether (15 ml), and lithium (0.33 g, 0.048 gram atom) was added to the solution, followed by stirring to effect a reaction under reflux for 4 hr. After completion of the reaction, the reaction mixture was cooled and an anhydrous diethyl ether solution (12 ml) of a compound (4.1 g, 0.022 mol) having the formula

O=⬡—⌬—CH₃ was added dropwise to the cooled reaction mixture at 10°-15° C., followed by reaction at room temperature (25° C.) for 30 min. After adding the reaction mixture to at 10°-15° C., followed by reaction at room temperature (25° C.) for 30 min. After adding the reaction mixture to cold water, the reaction product was extracted with toluene. The extract was washed with water and dried. By distilling off the solvent, a crude product containing a compound having the structure shown below was obtained in an amount of 8.7 g.

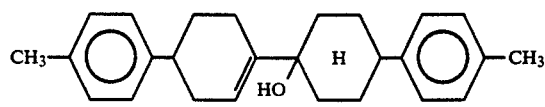

Sodium iodide (13 g, 0.087 mol) was dissolved in acetonitrile (52 mol) and chlorotrimethylsilane (9.4, 0.087 mol) was added dropwise to this solution. To the resulting solution, a toluene solution (30 ml) of the previously obtained crude product was added dropwise with stirring at 5°-10° C., followed by reaction at the same temperature for 1 h. To the reaction mixture, DBU (16 g, 0.110 mol) was added dropwise at 10°-20° C. and stirred at room temperature (25° C.) for 15 h. Water was added to the reaction mixture and the reaction product was extracted with toluene. The extract was successively washed with dilute HCl, a saturated acidic aqueous solution of sodium sulfite, a saturated aqueous solution of sodium hydrogencarbonate and a saturated aqueous solution of sodium chloride, and subsequently dried. By distilling off the solvent, a crude reaction product was obtained. This crude reaction product was purified by column chromatography on silica gel and further purified by recrystallization from n-hexane to obtain a compound having the structure shown below in an amount of 3.7 g (0.011 mol):

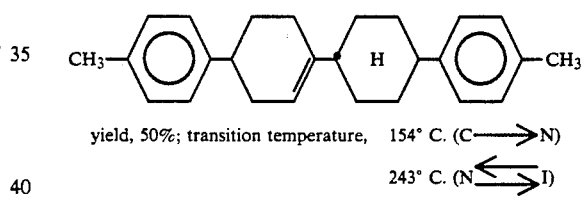

yield, 50%; transition temperature, 154° C. (C⟶N)
243° C. (N⇌I)

EXAMPLE 4

The procedures of Example 3 were repeated except that the compound of formula

was replaced by a compound of formula

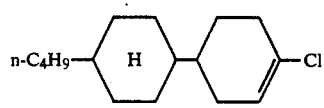

and that the compound of formula

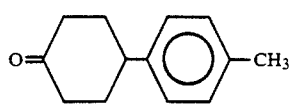

was replaced by a compound of the formula

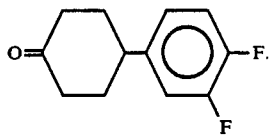

As a result, a mixture of two compounds having the structures shown below was obtained (yield 43%). This mixture showed a nematic phase between 160° C. and 239° C.

By column chromatography on silica gel, the individual components of the mixture were isolated. Thereafter, the isolated components were purified by recrystallization from a mixed solvent of n-hexane and ethanol to obtain the desired compounds.

|  | Transition temperature |
| --- | --- |
| 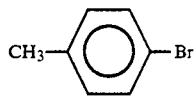 | 60° C. (C ⟶ S) |
|  | 160° C. (S ⇌ N) |
|  | 244° C. (N ⇌ I) |
|  | 64° C. (C ⟶ S) |
|  | 170° C. (S ⇌ N) |
|  | 238° C. (N ⇌ I) |

EXAMPLE 5

A compound (28.0 g, 0.163 mol) having the formula

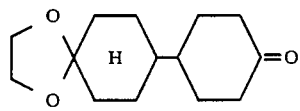

dissolved in anhydrous THF (112 ml) and the solution was added dropwise to magnesium powder (4.36 g, 0.0255 gram atom) with stirring at 20°–30° C. By further reaction at room temperature (25° C.) for 2 hr, a compound represented by the formula CH₃—⟨O⟩—MgBr was obtained.

A solution of a compound of the formula (30.0 g, 0.126 mol) in anhydrous THF (60 ml) was added dropwise to the above prepared Grignard reagent with stirring at 7°–23° C., followed by reaction for another 1° h at room temperature. After completion of the reaction, the reaction mixture was added to a saturated solution of ammonium chloride and the reaction product was extracted with toluene. The extract was washed with water and dried. By distilling off the solvent from the dried solution, a crude product containing a compound having the structure shown below was obtained in an amount of 46.5 g:

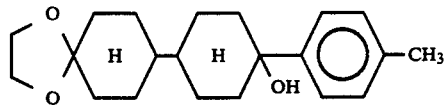

This crude product was dissolved in toluene (250 ml) and p-toluenesulfonic acid monohydrate (0.24 g, 1.3 mol) was added to the solution and subjected to a dehydration reaction under reflux for 1 h with stirring. After cooling the reaction mixture, the toluene layer was successively washed with a saturated aqueous solution of sodium hydrogencarbonate and a saturated aqueous solution of sodium chloride, and subsequently dried. The reaction product obtained by distilling off toluene was recrystallized from ethanol to obtain the pure form of a compound having the structure shown below in an amount of 25.0 g (0.0801 mol); yield 64%:

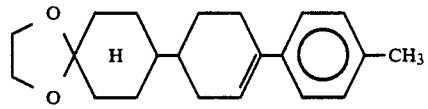

This compound was dissolved in a mixed solvent of ethanol (50 ml) and ethyl acetate (50 ml). A catalytic amount of Raney nickel was added to the solution, which was stirred at 60°–70° C. under pressure (≦3.0 g/cm²) to perform a hydrogenation reaction. After completion of the reaction, the reaction mixture was filtered to remove the catalyst and the solvent was distilled off from the filtrate. The resulting crude product was recrystallized from ethanol to obtain the pure form of a compound (11.0 g, 0.035 mol) having the structure shown below (yield 44%):

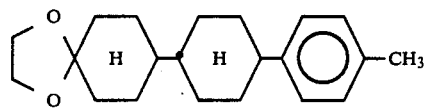

This compound was dissolved in toluene (50 ml) and a mixture of 10% sulfuric acid (50 ml) and acetic acid (20 ml) was added to the solution, followed by reaction with stirring for 5 h under reflux. After completion of the reaction, the reaction mixture was cooled and the toluene layer was washed with water and dried, followed by removal of toluene by distillation. The obtained crude product was purified by recrystallization from a mixed solvent of n-hexane and ethanol to obtain 8.6 g (0.032 mol) of a compound having the structure shown below (yield 90%):

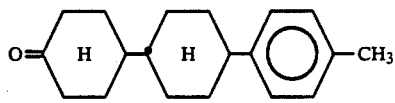

In the next step, a compound (4.2 g, 0.026 mol) represented by the formula

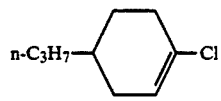

was dissolved in anhydrous diethyl ether (13 ml). Lithium (0.36 g, 0.052 gram atom) was added to the solution, which was stirred for reaction under reflux for 4 h. After completion of the reaction, the reaction mixture was cooled and an anhydrous 1,2-dimethoxyethane solution (50 ml) of the previously obtained compound of the formula

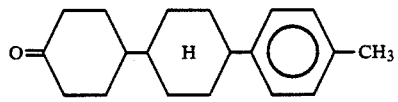

(6.0 g, 0.022 wmol) was added dropwise to this reaction mixture at −13° to 0° C., followed by reaction at room temperature for 30 min. After adding the reaction mixture to cold water, the reaction product was extracted with toluene and the extract was washed with water and dried. By distilling off the solvent, a crude product containing a compound having the structure shown below was obtained in an amount of 10 g:

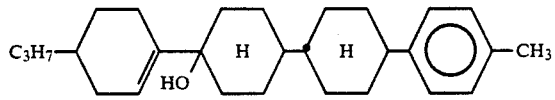

Sodium iodide (13 g, 0.087 mol) was dissolved in acetonitrile (52 ml) and chlorotrimethylsilane (9.4 g, 0.087 mol) was added dropwise to this solution. The resulting solution, a toluene solution (40 ml) of the previously obtained crude product was added dropwise with stirring at 5°–10° C., followed by reaction at the same temperature for 30 min. To the reaction mixture, DBU (15 g, 0.099 wmol) was added dropwise at 7°–18° C., followed by reaction at room temperature (25° C.) for 5 hr, then under reflux for 1 hr. After cooling the reaction mixture, dilute HCl was added and the reaction product was extracted with toluene. The extract was successively washed with dilute HCl, a saturated acidic aqueous solution of sodium sulfite, a saturated aqueous solution of sodium hydrogencarbonate and a saturated aqueous solution of sodium chloride, and subsequently dried. By distilling off the solvent, a crude reaction product was obtained.

This crude reaction product was purified by column chromatography on silica gel and further purified by recrystallization from a mixed solvent of n-hexane and ethanol so as to obtain a mixture (4.2 g, 0.011 mol) of two compounds having the structures shown below;

yield 50%. This mixture showed a nematic phase between 240° and 285° C.

By high-pressure liquid chromatography, the individual components of the mixture were separated. Thereafter, the separated components were purified by recrystallization from a mixed solvent of n-hexane and ethanol to obtain the desired compounds.

| | Transition temperature |
|---|---|
| 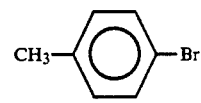 | 240° C. (S ⇌ N) |
| | 290° C. (N ⇌ I) |
| 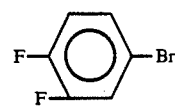 | 250° C. (S ⇌ N) |
| | 282° C. (N ⇌ I) |

EXAMPLE 6

The procedures of Example 5 were repeated except that the compound of the formula

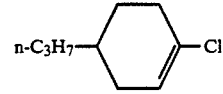

replaced by a compound (31.5 g) of the formula

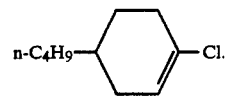

and that the compound of the formula was replaced by a compound of the formula

As a result, a mixture of two compounds having the structures shown below was obtained. This mixture showed a nematic phase between 148° and 236° C.

This mixture was separated into the respective components and purified as in Example 5 to obtain the desired compounds.

| | Transition temperature | |
|---|---|---|
| 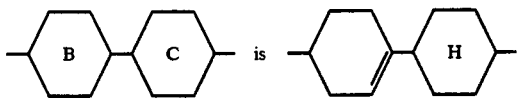 | 148° C. | (S ⇌ N) |
| | 241° C. | (N ⇌ I) |
| 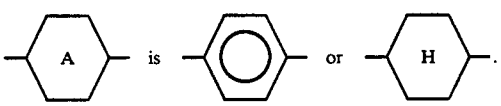 | 158° C. | (S ⇌ N) |
| | 235° C. | (N ⇌ I) |

The compound of formula (I) of the present invention has a nematic phase in the high temperature range and the lower limit of the temperature range for the appearance of a nematic phase is lower than in the case of known compounds having similar structures. Therefore, by mixing this compound with a nematic mixed liquid crystal which is commercially used today as a host liquid crystal, the N-I point of the mixed liquid crystal can be elevated and at the same time, the appearance of a crystalline or smectic phase in the mixed liquid crystal in the low temperature range can be prevented.

While the invention has been described in detail and with reference to specific embodiments thereof, it will be apparent to one skilled in the art that various changes and modifications can be made therein without departing from the spirit and scope thereof.

What is claimed is:

1. A compound represented by the general formula:

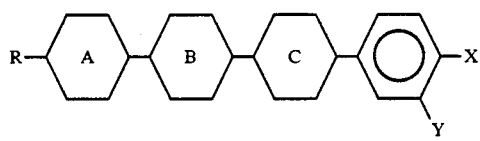

where R is a straight-chained alkyl group having 1–9 carbon atoms; and

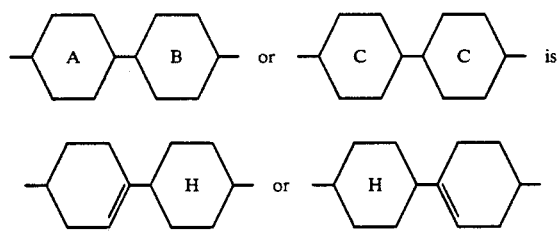 is

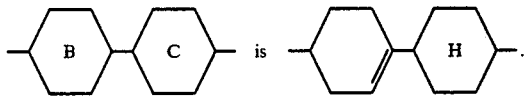

and the other ring is

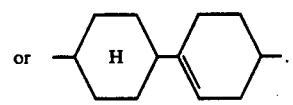 or 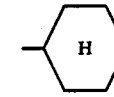, X is a fluorine atom or a straight-chained alkyl group having 1–9 carbon atoms, and Y is a hydrogen or fluorine atom.

2. A compound according to claim 1 wherein

—[B]—[C]— is —[⬡=H]— or —[H=⬡]—.

3. A compound according to claim 2, wherein

—[A]— is —[⌬]— or —[H]—.

4. A compound according to claim 3, wherein Y is a hydrogen atom.

5. A compound according to claim 4, wherein X and R are both a methyl group.

6. A compound according to claim 3, wherein X and Y are both a fluorine atom.

7. A compound according to claim 6, wherein R is a n-butyl group.

8. A compound according to claim 1, wherein

—[B]—[C]— is —[⬡=H]—.

9. A compound according to claim 8, wherein Y is a hydrogen atom, and X is a straight-chained alkyl group having 1–9 carbon atoms.

10. A compound according to claim 8, wherein X and Y are both a fluorine atom.

11. A compound according to claim 10, wherein R is a n-butyl group.

12. A compound according to claim 9, wherein X and R are each a methyl group.